(12) United States Patent
Kong et al.

(10) Patent No.: US 8,084,657 B2
(45) Date of Patent: Dec. 27, 2011

(54) INTEGRATED PROCESS FOR THE PRODUCTION OF P-XYLENE

(75) Inventors: Dejin Kong, Shanghai (CN); Hongli Guo, Shanghai (CN); Luping Zhong, Shanghai (CN); Weisheng Yang, Shanghai (CN); Jian Xiao, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 245 days.

(21) Appl. No.: 12/622,974

(22) Filed: Nov. 20, 2009

(65) Prior Publication Data
US 2010/0228066 A1   Sep. 9, 2010

(30) Foreign Application Priority Data
Mar. 9, 2009   (CN) .......................... 2008 1 0043974

(51) Int. Cl.
*C07C 5/27*   (2006.01)
*C07C 6/12*   (2006.01)
*C07C 4/12*   (2006.01)
(52) U.S. Cl. ........ 585/319; 585/477; 585/470; 585/483; 585/820; 585/812
(58) Field of Classification Search .................. 585/319, 585/470, 477, 483, 820, 812
See application file for complete search history.

(56) References Cited

U.S. PATENT DOCUMENTS
3,948,758 A * 4/1976 Bonacci et al. ............... 585/474
* cited by examiner

*Primary Examiner* — Thuan Dinh Dang
(74) *Attorney, Agent, or Firm* — Cozen O'Connor (57) ABSTRACT

A process of making p-xylene comprising processing a mixed feedstock containing benzene, toluene, $C_8$ aromatic hydrocarbons, $C_9$ and higher aromatic hydrocarbons, and non-aromatic hydrocarbons through a series of operations and various units, including a $C_9$ and higher aromatic hydrocarbon dealkylation unit, a toluene selective disproportionate unit, an adsorption separation unit, an isomerization unit, and a crystallization separation unit.

8 Claims, 2 Drawing Sheets

Fig. 3

INTEGRATED PROCESS FOR THE PRODUCTION OF P-XYLENE

CROSS REFERENCE OF RELATED APPLICATION

The present application claims the benefit of Application No. CN200810043974.2, filed on Mar. 9, 2009, which is incorporated herein by reference in its entirety and for all purposes.

TECHNICAL FIELD

The present invention relates to an integrated process for the production of p-xylene.

BACKGROUND ART

P-xylene (PX) is one of basic organic feedstock's in petrochemical industry, and finds widespread use in the production of various chemicals such as chemical fibers, synthetic resins, agrochemicals and medicines. P-xylene is typically produced from an ethylbenzene-containing xylene stream, i.e., $C_8$ aromatic hydrocarbon stream ($C_8A$), in thermodynamic equilibrium derived from catalytic reforming of naphtha, wherein p-xylene is separated from a mixture of isomers having similar boiling points through a multi-stage cryogenic crystallization separation technique or a simulated moving bed molecular sieve adsorption separation (briefly referred to as adsorption separation) technique. The separated o- and m-xylenes are generally isomerized into p-xylene through a $C_8A$ isomerization (briefly referred to as isomerization) technique. Disproportionation of toluene or disproportionation and transalkylation of toluene and $C_9^+$ aromatic hydrocarbons (briefly referred to as toluene disproportionation and transalkylation) may be utilized to produce benzene and $C_8A$, thereby obtaining even more p-xylene.

Until now, the relatively well-developed processes associated with toluene disproportionation include conventional Tatoray toluene disproportionation process as industrialized at the end of 1960's, MTDP process as put forward at the end of 1980's, and S-TDT process and TransPlus process as put forward in recent years. Toluene selective disproportionation is a new route for the production of p-xylene, wherein toluene undergoes selective disproportionation over a modified ZSM-5 catalyst to produce benzene and $C_8A$ with a high concentration of p-xylene, and a majority of p-xylene can be separated through only a simple step of freezing separation. In recent years, as the performance of the catalysts is continuously improved, this process is significantly developed. It is represented by MSTDP toluene selective disproportionation process as industrialized in the later stage of 1980's and pX-Plus process as put forward in recent years.

The MSTDP toluene selective disproportionation process comprises treating a toluene feedstock with a modified ZSM-5 mesoporous molecular sieve catalyst, to produce $C_8A$ with a high concentration of p-xylene (85-90%, by weight, the same below unless otherwise specified) and nitration grade benzene. The pX-Plus process, of which industrial application has not been reported, has the following main technical parameters: in the case of a toluene conversion of 30%, the selectivity of PX in xylenes reaches 90%, and the molar ratio of benzene to PX is 1.37.

However, such toluene selective disproportionation processes have a strict requirement on the selection of feedstock while having a high para-selectivity. These processes can only employ toluene as the feedstock, and $C_9^+A$ cannot be used (at least cannot be directly used) in these processes, resulting in the waste of aromatic hydrocarbon resources. Furthermore, these processes produce a large quantity of benzene as by-product, resulting in a relatively low yield of p-xylene, which is a fatal shortcoming of the selective disproportionation processes.

Typical feed to a reactor in Tatoray process comprises toluene and $C_9$ aromatic hydrocarbons ($C_9A$). The xylene produced by Tatoray process is a mixture of isomers in thermodynamic equilibrium, wherein the content of p-xylene that is the most valuable in industry is generally only about 24%. It is undoubted that Tatoray process possesses an obvious disadvantage relative to the toluene selective disproportionation processes that can produce mixed xylenes having a p-xylene concentration of about 90%. However, relative to the toluene selective disproportionation processes, Tatoray process has a great advantage that it is capable of converting $C_9A$ into benzene and xylenes. Literatures relating to Tatoray process include, for example, U.S. Pat. No. 4,341,914, CN98110859.8, U.S. Pat. No. 2,795,629, U.S. Pat. No. 3,551,510, and CN97106719.8. A representative process as set forth in U.S. Pat. No. 4,341,914 comprises the steps of subjecting a reformed product to fractionation of aromatic hydrocarbons; feeding the resulting toluene and $C_9A$ to a Tatoray process unit for disproportionation and transalkylation; separating a reaction effluent; recycling toluene, $C_9A$ and a portion of $C_{10}$ aromatic hydrocarbons ($C_{10}A$), and collecting benzene as a product; passing $C_9$ aromatic hydrocarbons together with additional $C_8$ aromatic hydrocarbons from an isomerization unit to a PX separation unit to separate a high purity p-xylene product; and passing other $C_8$ aromatic hydrocarbon isomers to the isomerization unit for isomerization of xylene, to obtain mixed xylenes in thermodynamic equilibrium again.

In recent years, as the rising of the toluene selective disproportionation processes, a process for the production of $C_6$-$C_8$ aromatic hydrocarbons by dealkylation of heavy aromatic hydrocarbons draws more and more attention. U.S. Pat. No. 5,763,721 and U.S. Pat. No. 5,847,256 respectively propose catalysts useful in the dealkylatoin of heavy aromatic hydrocarbons. Among these, U.S. Pat. No. 5,847,256 discloses a rhenium-containing mordenite catalyst, which is especially suitable for the conversion of feedstock enriched in aromatic hydrocarbons having one or more ethyl groups to form toluene, xylenes, benzene, etc.

The various $C_8$ aromatic hydrocarbons have similar boiling points: 136.2° C. for ethylbenzene, 138.4° C. for p-xylene, 139.1° C. for m-xylene, and 144.4° C. for o-xylene. O-xylene having the highest boiling point can be separated by rectification process, which however requires more than one hundred of theoretical plates and a relatively great reflux ratio. Ethylbenzene having the lowest boiling point can also be separated by rectification process, which however is much more difficult. The various $C_8$ aromatic hydrocarbons have markedly different melting points: 13.3° C. for p-xylene, −25.2° C. for o-xylene, −47.9° C. for m-xylene, and −94.95° C. for ethylbenzene. P-xylene has the highest melting point, and can be separated by crystallization process. If the concentration of p-xylene in the feedstock is not high, a two-stage crystallization process is generally employed in order to achieve an industrially acceptable yield. The process disclosed in U.S. Pat. No. 3,177,255 and U.S. Pat. No. 3,467,724 comprises the steps of: crystallizing most of p-xylene at a low temperature of −80 to −60° C., to achieve a yield close to the maximum theoretical yield, the crystal obtained having a purity of 65 to 85%; melting the crude xylene crystal followed by a second crystallization at a temperature of generally −20 to 0° C., to obtain p-xylene with a purity of above 99%; and recycling the mother liquor from the second crystallization, which has a relatively high p-xylene level, to the first crystallization stage.

By virtue of the difference in selectivity of an adsorbent for various $C_8$ aromatic hydrocarbons, p-xylene can be separated by an adsorption separation process. This process has become one of the major processes for the production of p-xylene once it has been industrialized in 1970's. U.S. Pat. No. 2,985,589 describes a process for the separation of p-xylene by using a countercurrent simulated moving bed; U.S. Pat. No. 3,686,342, U.S. Pat. No. 3,734,974 and CN98810104.1 describe the use of Ba-type or Ba and K-type X or Y zeolite as an absorbent in adsorption separation; U.S. Pat. No. 3,558,732 and U.S. Pat. No. 3,686,342 respectively describe the use of toluene and p-diethylbenzene as a strippant in adsorption separation.

SUMMARY OF THE INVENTION

In order to overcome the problem regarding a large circulation quantity and a high energy consumption in xylene separation unit and isomerization unit due to a low concentration of p-xylene in mixed xylenes or regarding a low overall yield of p-xylene, suffered by the existing techniques for the production of p-xylene, the inventors made diligently studies. As a result, the present invention provides a new integrated process for the production of p-xylene, which can increase the concentration of p-xylene in mixed xylenes, reduce the scale of p-xylene separation unit, isomerization unit and aromatic hydrocarbon fractionation unit to a relatively great extent, to thereby reduce the energy consumption of the whole equipment, and provide p-xylene at a high overall yield.

An object of the invention is to provide an integrated process for the production of p-xylene, comprising the steps of A) separating a mixed feedstock containing benzene, toluene, $C_8$ aromatic hydrocarbons, $C_9$ and higher aromatic hydrocarbons, and non-aromatic hydrocarbons from a reforming unit, to obtain a first benzene stream, a first toluene stream, a first $C_8$ aromatic hydrocarbon stream, a stream of $C_9$ and higher aromatic hydrocarbons, and a stream of non-aromatic hydrocarbons;

B) feeding the stream of $C_9$ and higher aromatic hydrocarbons from step A) to a $C_9$ and higher aromatic hydrocarbon dealkylation unit, where dealkylation reaction occurs in the presence of hydrogen, and separating the reaction effluent to obtain a second benzene stream, a second toluene stream, and a second $C_8$ aromatic hydrocarbon stream;

C) feeding both the first toluene stream and the second toluene stream to a toluene selective disproportionation unit, where toluene selective disproportionation reaction occurs in the presence of hydrogen to produce a stream containing $C_8$ aromatic hydrocarbons including p-xylene and benzene, which stream is separated to obtain a third $C_8$ aromatic hydrocarbon stream, a third toluene stream, and a third benzene stream, with the third toluene stream being returned to an inlet of this unit;

D) feeding both the first $C_8$ aromatic hydrocarbon stream and the second $C_8$ aromatic hydrocarbon stream to an adsorption separation unit, to obtain a first p-xylene product stream and a fifth $C_8$ aromatic hydrocarbon stream, with the fifth $C_8$ aromatic hydrocarbon stream being passed to an isomerization unit;

E) feeding the third $C_8$ aromatic hydrocarbon stream to a crystallization separation unit, to obtain a fourth $C_8$ aromatic hydrocarbon stream and a second p-xylene product stream, with the fourth $C_8$ aromatic hydrocarbon stream being passed to the adsorption separation unit or the isomerization unit; and F) feeding an effluent of the isomerization unit to an inlet of the adsorption separation unit.

DESCRIPTION OF PREFERRED EMBODIMENTS

In step A) of the present process, a conventional technique is used to separate a mixed feedstock containing benzene, toluene, $C_8$ aromatic hydrocarbons, $C_9$ and higher aromatic hydrocarbons ($C_9^+A$, also referred to as heavy aromatic hydrocarbons hereinafter), and non-aromatic hydrocarbons from a reforming unit, to obtain benzene, toluene, $C_8$ aromatic hydrocarbons, $C_9$ and higher aromatic hydrocarbons, and non-aromatic hydrocarbons. Such a technique and processing conditions employed therein are well known to a person skilled in the art.

In step B) of the present process, $C_9$ and higher aromatic hydrocarbons are subjected to dealkylation reaction over a dealkylation catalyst in the presence of hydrogen in a $C_9^+A$ dealkylation unit, to produce benzene, toluene, and $C_8A$. Toluene separated from the reaction effluent is fed to a toluene selective disproportionation unit. Benzene separated from the reaction effluent may be collected as a product or circulated in this unit. Preferably, at least a portion of the benzene is circulated in this unit, and this can reduce the formation of benzene as a by-product in the dealkylation reaction. $C_8A$ separated from the reaction effluent is fed to an adsorption separation unit, to produce pure p-xylene and a $C_8A$ stream mainly composed of m-xylene and o-xylene, which $C_8A$ stream is fed to an isomerization unit.

In step B) of the present process, any of the catalysts for dealkylating aromatic hydrocarbons known in the art can be used. In an embodiment, the catalyst used in the $C_9^+A$ dealkylation unit is a molecular sieve catalyst containing bismuth and/or its oxide in an amount of from 0.005 to 5 wt %, wherein the molecular sieve is at least one selected from the group consisting of β-zeolite, mordenite and MCM-22.

In an embodiment, the $C_9^+A$ dealkylation unit is operated under the following conditions: a reaction pressure of from 1 to 5 MPa (absolute, the same below), a reaction temperature of from 250 to 480° C., a molar ratio of hydrogen to hydrocarbons of from 0.5:1 to 8:1, and a weight hourly space velocity of from 0.8 to 10 $hr^{-1}$.

In step C) of the present process, both the toluene obtained from the $C_9^+A$ dealkylation unit and the toluene obtained from step A) are fed to a toluene selective disproportionation unit, where toluene selective disproportionation reaction occurs in the presence of a toluene selective disproportionation catalyst. From the reaction effluent, a benzene stream and a $C_8A$ stream with a high concentration of p-xylene (which may be up to 80 to 95%) are separated. This $C_8A$ stream is sent to a crystallization separation unit to separate pure p-xylene, and the remaining of this $C_8A$ stream is sent to the adsorption separation unit to obtain pure p-xylene, or to the isomerization unit to obtain a mixed xylene stream having a thermodynamic equilibrium composition.

In step C) of the present process, any of toluene selective disproportionation catalysts known in the art can be used. In an embodiment, the catalyst used in the toluene selective disproportionation unit is a ZSM-5 molecular sieve catalyst containing at least one metal selected from platinum, molybdenum and magnesium and/or oxides thereof in an amount of from 0.005 to 5 wt %. Preferably, the toluene selective disproportionation catalyst used is a ZSM-5 molecular sieve catalyst containing platinum and/or its oxides in an amount of from 0.005 to 5 wt %.

In an embodiment, the toluene selective disproportionation unit is operated under the following conditions: a reaction pressure of from 1 to 4 MPa, a reaction temperature of from 300 to 480° C., a molar ratio of hydrogen to hydrocarbons of from 0.5:1 to 10:1, and a weight hourly space velocity of from 0.8 to 8 $h^{-1}$.

In the present process, p-xylene is separated in the p-xylene separation unit by means of adsorption separation in combination with crystallization separation. The $C_8A$ stream having a high concentration of p-xylene is separated by means of crystallization separation, whereby the separation can be fulfilled with a high efficiency at a low cost. The $C_8A$ stream having a concentration of p-xylene close to equilibrium concentration is separated by means of adsorption separation, whereby pure p-xylene can be obtained directly. The crystallization separation can be accomplished by falling-film crystallization separation or suspension crystallization separation. The crystallization temperature in falling-film crystallization separation is from −80 to 5° C. In suspension crystallization separation, the crystallization temperature is from −80 to 5° C., the weight ratio of washing liquid to crystal is from 0.05:1 to 0.5:1. The adsorption separation process as well as the adsorbents and processing conditions used therein is well known to a person skilled in the art.

In the present process, the isomerization unit can be operated under the conditions well known to a person skilled in the art, and effluent from the isomerization unit may be fed to the adsorption separation unit to obtain additional pure p-xylene, and/or to the catalytic reforming unit.

The present process not only makes well use of $C_9^+A$ resources, but also greatly increases the concentration of p-xylene in the mixed xylene produced, to thereby decrease the processing scales of the isomerization unit and the adsorption separation unit, effectively reduce the energy consumption and the equipment investment, lower the production cost, and achieve a preferable technical effect.

Figure 1:
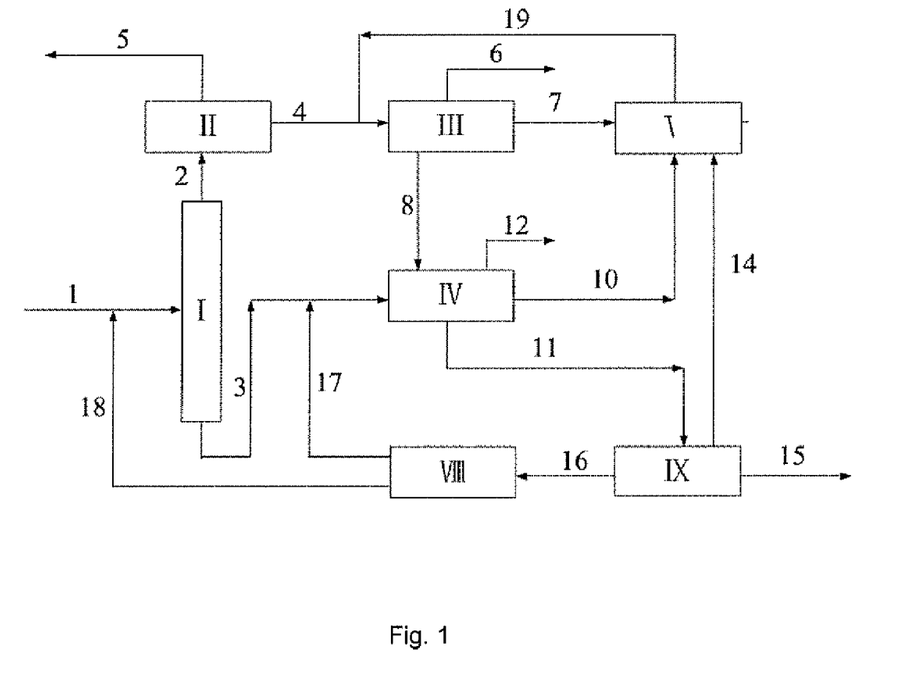
FIG. 1 depicts a conventional process for the production of p-xylene.
Figure 2:
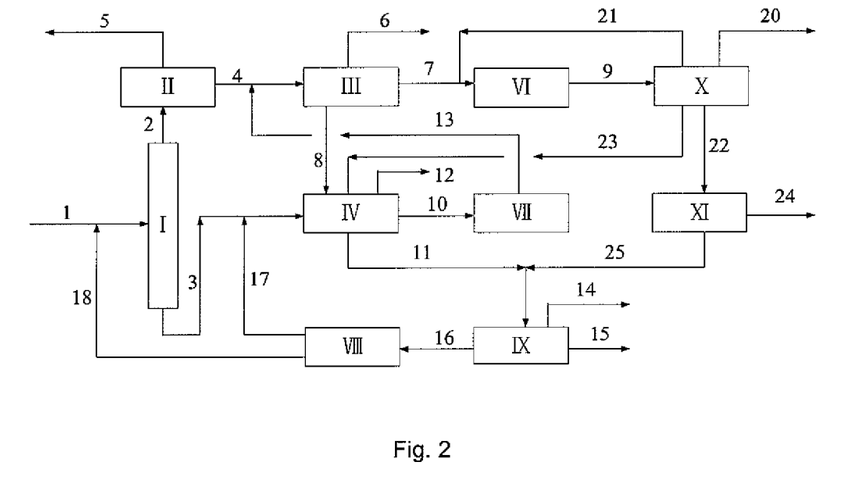
FIGS. 2 and 3 depict the integrated processes for the production of p-xylene according to the invention.
Figure 3:
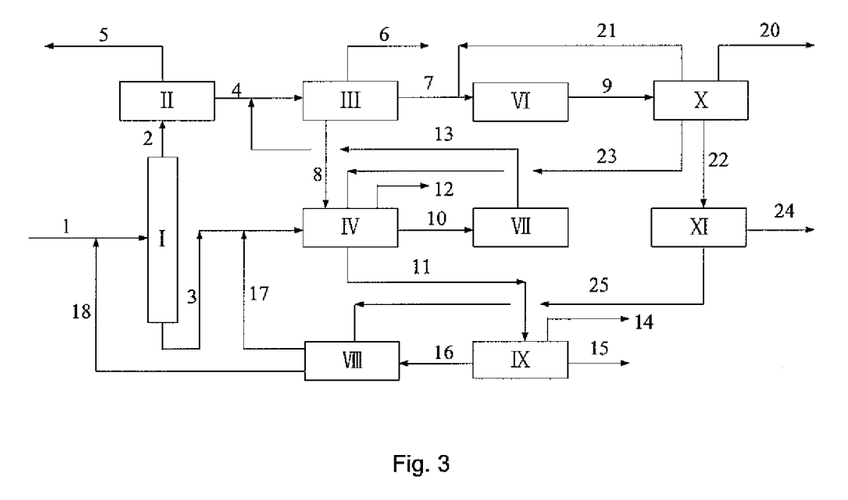

The preferred embodiments of the present invention will be further described in detail by reference to the figures. FIG. 1 shows a conventional process for the production of p-xylene. FIGS. 2 and 3 show integrated processes for the production of p-xylene according to the present invention.

In FIG. 1, 2 or 3, I represents a deheptanizing column of a reforming unit; II represents an aromatic hydrocarbon extraction unit; III represents a benzene/toluene separation unit, including a benzene column and a toluene column; IV represents a $C_8$ and higher aromatic hydrocarbons ($C_8^+A$) separation unit, including a heavy aromatic hydrocarbon column and a xylene column; V represents a toluene disproportionation and transalkylation unit; VI represents a toluene selective disproportionation unit; VII represents a heavy aromatic hydrocarbon dealkylation unit, including a dealkylation reactor and a benzene column; VIII represents a xylene isomerization unit, including an isomerization reactor and a deheptanizing column of isomerization unit; IX represents an adsorption separation unit; X represents an aromatic hydrocarbon fractionation unit for separating toluene selective disproportionation product, including a benzene column, a toluene column, and a xylene column; and XI represents a crystallization separation unit. 1 represents a reformed depentanized oil; 2 represents a stream of $C_7^-$ (including benzene, toluene, and $C_6$ and $C_7$ non-aromatic hydrocarbons) withdrawn from the top of the deheptanizing column; 3 represents a $C_8^+A$ stream withdrawn from the bottom of the deheptanizing column; 4 represents a stream of benzene and toluene remained after extracting non-aromatic hydrocarbons; 5 represents a non-aromatic hydrocarbons stream; 6 represents a high purity benzene product withdrawn from the top of the benzene column; 7 represents toluene withdrawn from the top of the toluene column; 8 represents $C_8^+A$ withdrawn from the bottom of the toluene column; 9 represents a product stream from the toluene selective disproportionation unit; 10 represents $C_9A$ and a portion of $C_{10}A$ withdrawn from the top of the heavy aromatic hydrocarbon column in the $C_8^+A$ separation unit; 11 represents mixed xylenes withdrawn from the top of the xylene column; 12 represents $C_{10}^+A$ withdrawn from the bottom of the heavy aromatic hydrocarbon column; 13 represents a residue withdrawn from the bottom of the benzene column in the heavy aromatic hydrocarbon dealkylation unit; 14 represents a minor quantity of toluene separated from the adsorption separation unit; 15 represents pure p-xylene separated from the adsorption separation unit; 16 represents a mixed xylenes stream remained after the adsorption separation of PX; 17 represents a $C_8^+A$ stream withdrawn from the bottom of the deheptanizing column in the isomerization unit; 18 represents a stream containing benzene and toluene withdrawn from the top of the deheptanizing column in the isomerization unit; 19 represents a product stream withdrawn from the disproportionation and transalkylation unit; 20 represents a benzene stream withdrawn from the top of the benzene column in the selective disproportionation unit; 21 represents a toluene stream withdrawn from the top of the toluene column in the selective disproportionation unit; 22 represents a $C_8A$ stream withdrawn from the top of the xylene column in the selective disproportionation unit; 23 represents a residue withdrawn from the bottom of the xylene column in the selective disproportionation unit; 24 represents a stream of pure p-xylene separated from the crystallization separation unit; and 25 represents a mixed xylenes stream remained after the crystallization separation of PX.

A conventional process for the production of p-xylene is shown in FIG. 1. The bottoms 1 from the depentanizing column in the reforming unit are fed to the deheptanizing column I, from the top of which the stream 2 of $C_7$ and lower aromatic hydrocarbons and non-aromatic hydrocarbons is withdrawn. The stream 2 is fed to the aromatic hydrocarbon extraction unit II to separate the aromatic hydrocarbons from the non-aromatic hydrocarbons, with the non-aromatic hydrocarbons steam 5 separated being discharged, and the benzene/toluene stream 4 being fed to the benzene/toluene separation unit III. The benzene product stream 6 is withdrawn from the top of the benzene column in the unit III, and the mixed xylenes stream 8 is withdrawn from the bottom of the toluene column in the unit III. The stream 8 and the stream 3 from the bottom of the deheptanizing column are fed to the $C_8^+A$ separation unit IV. The steam of mixed xylenes 11 is withdrawn from the top of the xylene column in the unit IV, and then fed to the p-xylene adsorption separation unit IX. The $C_9A$-containing stream 10 from the $C_9^+A$ separation unit IV and the toluene stream 7 from the top of the toluene column are sent as a feedstock to the toluene disproportionation and transalkylation unit V. The $C_{10}^+A$ stream 12 from the $C_8^+A$ separation unit IV is discharged as a by-product. The product stream 19 from the toluene disproportionation and transalkylation unit V is directly fed to the unit III for separation. From the adsorption separation unit IX, the stream 15 of p-xylene as the target product, a minor amount of toluene stream 14 and the stream 16 of a mixture of other xylenes are obtained. The toluene stream 14 is returned to the toluene disproportionation unit V, and the stream 16 of other mixed xylenes is fed to the xylene isomerization unit VIII for isomerization. The $C_8^+A$ stream 17 withdrawn from the bottom of the deheptanizing column in the isomerization unit is sent to the $C_8^+A$ separation unit IV, and the stream 18 containing benzene and toluene withdrawn from the top of the deheptanizing column is sent to the catalytic reforming unit.

The integrated processes for the production of p-xylene according to the present invention are shown in FIGS. 2 and 3. As compared with the conventional process shown in FIG. 1, the modifications of the present processes are: (1) the toluene disproportionation unit in the conventional process is changed to the heavy aromatic hydrocarbon dealkylation unit in the present processes; (2) the toluene selective disproportionation unit VI is added; and (3) the $C_8A$ stream is separated by means of crystallization separation or adsorption separation, depending on the concentration of p-xylene in the $C_8A$ stream, to obtain pure p-xylene. The difference between FIGS. 2 and 3 and FIG. 1 is described in detail below, while the commonness between them is not mentioned herein anymore. In the present processes, the $C_9^+A$ stream 10 that originally serves as a feedstock in the toluene disproportionation and transalkylation unit V is used as a feedstock in the heavy aromatic hydrocarbon dealkylation unit VII, and benzene produced in this dealkylation reaction is circulated within the unit. The $C_7^+A$ stream 13 obtained from the dealkylation unit VII is sent to the toluene column in the benzene/toluene separation unit III for separation. The toluene stream 7 (including toluene introduced by the feedstock and toluene produced by the heavy aromatic hydrocarbon dealkylation reaction) is used as a feedstock in the toluene selective disproportionation unit VI. The product stream 9 from the toluene selective disproportionation unit VI enters the aromatic hydrocarbon fractionation unit X, where the benzene stream 20 is withdrawn from the top of the benzene column, the toluene stream 21 is withdrawn from the top of the toluene column and sent back to the toluene selective disproportionation unit VI, the bottoms 23 is withdrawn from the bottom of the xylene column and sent to the $C_8^+A$ separation unit IV, and the $C_8A$ stream 22 is withdrawn from the top of the xylene column. The $C_8A$ stream 22 is sent to the crystallization separation unit XI, where the pure p-xylene stream 24 and the stream 25 of other mixed xylenes are obtained. The stream 25 is sent to the adsorption separation unit IX (as shown in FIG. 2) or to the isomerization unit VIII (as shown in FIG. 3).

EXAMPLES

The following examples are given for further illustrating the invention, but do not make limitation to the invention in any way.

Example 1

A $C_9^+A$ feedstock was obtained by separating a feedstock from a petrochemical aromatic hydrocarbon united plant. The $C_9^+A$ feedstock was subjected to dealkylation reaction in a fixed bed reactor in the presence of hydrogen. The reactor had an inner diameter of 25 mm and a length of 1000 mm, and was made of stainless steel. The reactor was packed with 20 g of a β-zeolite catalyst containing 0.05 wt % bismuth, which had been prepared by impregnating a powdery ammonium-form β-zeolite having a content of sodium oxide of 0.062 wt % and a molar ratio of silica to alumina of 30 with a 30 wt % aqueous solution of chemically pure bismuth nitrate, adding a 20 wt % aqueous solution of chemically pure nitric acid to the impregnated powder, sufficiently blending and homogenizing the mixture, extruding the mixture into strips, and calcining the extrudates at 550° C. for 4 hours to give the β-zeolite catalyst containing 0.05 wt % bismuth. Glass beads of φ3 mm were packed below and above the catalyst bed layer, to take the effect of distributing gas and supporting. The $C_9^+A$ feedstock was mixed with hydrogen and then passed through the catalyst bed layer downwards to perform dealkylation reaction of $C_9^+A$, thereby producing benzene, toluene, and $C_8A$. The reaction temperature was 425° C., the reaction pressure was 3.0 MPa, the weight hourly space velocity was 2.0 hr$^{-1}$, and the molar ratio of hydrogen/hydrocarbon was 5.0:1. The hydrogen was electrolytic hydrogen, and was subjected to a dehydration drying treatment before use. The reaction results are listed in Table 1.

TABLE 1

Compositions of the feedstock and the product involved in the dealkylation reaction of $C_9^+A$

| Components | NA | Ben | Tol | $C_8A$ | $C_9A$ | $C_{10}^+A$ | Σ |
| --- | --- | --- | --- | --- | --- | --- | --- |
| Feedstock, wt % | 0.00 | 0.00 | 0.01 | 0.82 | 93.24 | 5.93 | 100.00 |
| Product, wt % | 6.13 | 1.92 | 11.89 | 19.22 | 57.82 | 3.02 | 100.00 |

Notation:

NA represents non-aromatic hydrocarbons;

$C_{10}^+A$ represents $C_{10}$ or higher aromatic hydrocarbons;

Ben represents benzene;

Tol represents toluene;

$C_8A$ represents $C_8$ aromatic hydrocarbons; and $C_9A$ represents $C_9$ aromatic hydrocarbons.

It could be seen from the above experiment that the dealkylation reaction of the feedstock $C_9^+A$ produced benzene, toluene, and $C_8A$.

A toluene feedstock was obtained by separating a feedstock from a petrochemical aromatic hydrocarbon united plant. The toluene feedstock was subjected to toluene selective disproportionation reaction in a fixed bed reactor in the presence of hydrogen. The reactor had an inner diameter of 25 mm and a length of 1000 mm, and was made of stainless steel. The reactor was packed with 20 g of a ZSM-5 molecular sieve catalyst containing 0.05 wt % platinum, which had been prepared according to the process as described in CN 1340486A (Process for the preparation of catalysts for toluene selective disproportionation). Glass beads of φ3 mm were packed below and above the catalyst bed layer, to take the effect of distributing gas and supporting. The toluene feedstock was mixed with hydrogen and then passed through the catalyst bed layer downwards to perform toluene selective disproportionation reaction, thereby producing benzene and $C_8A$ consisting mainly of p-xylene. The hydrogen was electrolytic hydrogen, and was subjected to a dehydration drying treatment before use. The reaction temperature was 420° C., the reaction pressure was 1.5 MPa, the weight hourly space velocity was 4.0 hr$^{-1}$, and the molar ratio of hydrogen/hydrocarbon was 3.0:1. The reaction results are listed in Table 2.

TABLE 2

Results of the toluene selective disproportionation reaction

| Components | NA | Ben | Tol | PX | $C_8A^*$ | $C_9^+A$ | Σ |
|---|---|---|---|---|---|---|---|
| Product, wt % | 1.74 | 14.05 | 69.95 | 11.62 | 2.02 | 0.62 | 100.00 |

Notation:
$C_8A^*$ represents $C_8$ aromatic hydrocarbons other than PX, the same below;
PX represents p-xylene.

The product of the toluene selective disproportionation reaction was separated in an aromatic hydrocarbon fractionation unit, to obtain $C_8A$. The $C_8A$ was subjected to crystallization separation in a falling-film crystallizer. The falling-film crystallizer had an inner diameter of 25 mm, an outer diameter of 30 mm and a length of 500 mm, and was made of stainless steel. In the crystallizer, the feedstock went through the tube pass, and the cryogen went through the shell pass. The feedstock and the cryogen underwent countercurrent heat exchange in the crystallizer to perform crystallization separation, to thereby obtain a mother liquor, a sweating liquor, and pure p-xylene.

The crystallization separation process was carried out in the following three stages: 1) feeding the feedstock at a flow rate of 5 mL/min and a temperature of 25° C., and the cryogen at a flow rate of 50 mL/min and a temperature of −20° C., so as to crystallize p-xylene on the wall of the crystallizer and leave a mother liquor, with the feeding being stopped after 2 hours; 2) increasing the temperature of the cryogen to 20° C., whereby the crystal obtained was heated and partially melted to obtain a melt which was called as a sweating liquor, with the second stage being sustained for 15 min; and 3) increasing the temperature of the cryogen to 30° C. so as to melt totally the remaining crystal, to obtain pure p-xylene. The results of the falling-film crystallization separation process are listed in Table 3.

TABLE 3

Results of the falling-film crystallization separation process

| Components | Feedstock, wt % | Sweating liquor, wt % | Mother liquor, wt % | Product, wt % |
|---|---|---|---|---|
| PX | 85.15 | 96.73 | 42.51 | 99.84 |
| $C_8A^*$ | 14.85 | 3.27 | 57.49 | 0.16 |

Example 2

This experiment was performed by following the procedure as described in Example 1, except that the $C_8A$ obtained by separating the product of the toluene selective disproportionation reaction in an aromatic hydrocarbon fractionation unit was subjected to suspension crystallization separation. The suspension crystallizer had a volume of 500 L, was equipped with a jacket and a stirrer, and was made of stainless steel. The washing tower had a volume of 40 L, and was made of stainless steel. The feedstock was subjected to suspension crystallization in the crystallizer, and the slurry obtained after the crystallization was sent to the washing tower to perform solid-liquid separation and product purifying/washing.

The suspension crystallization separation process comprised a step of suspension crystallization and a step of washing/purifying. In the step of suspension crystallization, the feedstock was fed at a flow rate of 200 L/min and a temperature of 20° C., and the crystallization temperature was −5° C. In the step of washing/purifying, the washing liquid was fed at a flow rate of 15 L/min and a temperature of 20° C. The results of the suspension crystallization separation process are listed in Table 4.

TABLE 4

Results of the suspension crystallization separation process

| Components | Feedstock, wt % | Mother liquor, wt % | Product, wt % |
|---|---|---|---|
| PX | 85.15 | 63.37 | 99.84 |
| $C_8A^*$ | 14.85 | 36.63 | 0.16 |

Example 3

A typical reformed depentanized oil containing $C_6A$ to $C_{10}^+$ hydrocarbons was used as a feedstock to investigate the capacities of the present process as shown in FIG. 2 for the production of p-xylene and benzene and the processing scales of various units therein. The composition of the reformed depentanized oil and the flow rates of various components used in this Example are listed in Table 5.

TABLE 5

Composition of the reformed depentanized oil and flow rates of various components

| Components | Ben | Tol | $C_8A$ | $C_9A$ | $C_{10}^+$ | Σ |
|---|---|---|---|---|---|---|
| Content, wt % | 14.41 | 26.79 | 33.53 | 24.02 | 1.25 | 100.00 |
| Flow rate, Kg/hr | 12673 | 23560 | 29482 | 21122 | 1095 | 87932 |

Notation:
$C_{10}^+$ represents hydrocarbons having 10 or more carbon atoms.

The experiment was carried out by using the flow rates of aromatic hydrocarbons (fresh feed) as listed in Table 5 according to the process as shown in FIG. 2. The conditions and catalyst used in dealkylation reaction of $C_9^+A$, the conditions and catalyst used in toluene selective disproportionation reaction, and the conditions used in falling-film crystallization separation were the same as described in Example 1. The data regarding feed and discharge for toluene selective disproportionation unit, for $C_9^+A$ dealkylation unit, and for isomerization unit are listed in Table 6. The processing scales of various units in the equipment for the production of p-xylene are listed in Table 7. The yields of p-xylene and benzene as products are listed in Table 8.

The results demonstrate that, by using the present process, it is possible to use the aromatic hydrocarbon feedstock as listed in Table 5 to produce p-xylene and benzene at a total yield of the both of 78324 Kg/hr. As compared with the Comparative Example 1 below, the processing scales of xylene isomerization unit, adsorption separation unit and aromatic hydrocarbon fractionation unit are reduced by 26%, 27% and 27%, respectively. This implies that the design scale of the equipment can be notably decreased. The energy consumption of the equipment is $19890 \times 10^6$ J/ton of (p-xylene+benzene), which is reduced by 25% in relative to the energy consumption of $26579 \times 10^6$ J/ton of (p-xylene+benzene) in Comparison Example 1. Thus, the present invention overcomes the problems suffered by the existing techniques for the production of p-xylene that the concentration of p-xylene in mixed xylenes is low, that circulation quantity is large, and that energy consumption is high, and provides a new and economical process for the production of p-xylene.

TABLE 6

Materials in the process of Example 3

| Components | | Selective disproportionation unit | $C_9^+$ A dealkylation unit | Isomerization unit |
|---|---|---|---|---|
| Feed to the unit, Kg/hr | Ben | 14 | 0 | 0 |
| | Tol | 97617 | 0 | 108 |
| | $C_8A$ | 92 | 211 | 161632 |
| | $C_9A$ | 0 | 36715 | 87 |
| | $C_{10}^+A$ | 0 | 1824 | 0 |
| | Σ | 97723 | 38750 | 161827 |
| Discharge from the unit, Kg/hr | Ben | 13502 | 2 | 2069 |
| | Tol | 67233 | 5900 | 1038 |
| | PX | 12086 | 12011 | 155995 |
| | $C_8A^*$ | 1622 | | |
| | $C_9A$ | 791 | 14020 | 869 |
| | $C_{10}^+A$ | 0 | 3036 | 0 |
| | Σ | 95234 | 34969 | 157902 |

TABLE 7

Processing scales of various units in Example 3

| Name of unit | $C_9^+A$ de-alkylation unit | Isomer-ization unit | Adsorption separation unit | Crystal-lization separation unit | Aromatic hydrocarbon fractionation unit |
|---|---|---|---|---|---|
| Scale, Kg/hr | 38750 | 161209 | 201057 | 13708 | 235861 |

TABLE 8

Yield and purity of products in Example 3

| Product | p-xylene | Benzene | In total |
|---|---|---|---|
| Yield, Kg/hr | 49258 | 29066 | 78328 |
| Purity, % | 99.80 | 99.94 | |

Example 4

This experiment was carried out by using the flow rates of aromatic hydrocarbons (fresh feed) as listed in Table 5 according to the present process as shown in FIG. 2. The $C_8A$ obtained by separating the product of the toluene selective disproportionation reaction in an aromatic hydrocarbon fractionation unit was sent to a suspension crystallization separation unit to recover p-xylene. The conditions and catalyst used in dealkylation reaction of $C_9^+A$, the conditions and catalyst used in toluene selective disproportionation reaction, and the conditions used in suspension crystallization separation were the same as described in Examples 1 and 2. The processing scales of various units in the equipment for the production of p-xylene are listed in Table 9. The yields of p-xylene and benzene as products are listed in Table 10.

TABLE 9

Processing scales of various units in Example 4

| Name of unit | $C_9^+A$ de-alkylation unit | Isomer-ization unit | Adsorption separation unit | Crystal-lization separation unit | Aromatic hydrocarbon fractionation unit |
|---|---|---|---|---|---|
| Scale, Kg/hr | 38750 | 161532 | 203754 | 13708 | 245876 |

TABLE 10

Yield and purity of products in Example 4

| Product | p-xylene | Benzene | In total |
|---|---|---|---|
| Yield, Kg/hr | 49273 | 29067 | 78340 |
| Purity, % | 99.80 | 99.94 | |

The results demonstrate that, by using the present process, it is possible to use the aromatic hydrocarbon feedstock as listed in Table 5 to produce p-xylene and benzene at a total yield of the both of 78340 Kg/hr. As compared with the Comparative Example 1 below, the processing scales of xylene isomerization unit, adsorption separation unit and aromatic hydrocarbon fractionation unit are reduced by 26%, 26% and 24%, respectively. This implies that the design scale of the equipment can be notably decreased. The energy consumption of the equipment is $20465 \times 10^6$ Eton of (p-xylene+benzene), which is reduced by 23% in relative to the energy consumption of $26579 \times 10^6$ J/ton of (p-xylene+benzene) in Comparison Example 1.

Example 5

A typical reformed depentanized oil containing $C_6A$ to $C_{10}^+$ hydrocarbons was used as a feedstock to investigate the capacities of the present process as shown in FIG. 3 for the production of p-xylene and benzene and the processing scales of various units therein. The composition of the reformed depentanized oil and the flow rates of various components used in this Example are listed in Table 5.

The experiment was carried out by using the flow rates of aromatic hydrocarbons (fresh feed) as listed in Table 5 according to the process as shown in FIG. 3. The conditions and catalyst used in dealkylation reaction of $C_9^+A$, the conditions and catalyst used in toluene selective disproportionation reaction, and the conditions used in falling-film crystallization separation were the same as described in Example 1. The data regarding feed and discharge for toluene selective disproportionation unit, for $C_9^+A$ dealkylation unit, and for isomerization unit are listed in Table 11. The processing scales of various units in the equipment for the production of p-xylene are listed in Table 12. The yields of p-xylene and benzene as products are listed in Table 13.

The results demonstrate that, by using the present process, it is possible to use the aromatic hydrocarbon feedstock as listed in Table 5 to produce p-xylene and benzene at a total yield of the both of 78324 Kg/hr. As compared with the Comparative Example 1 below, the processing scales of xylene isomerization unit, adsorption separation unit and aromatic hydrocarbon fractionation unit are reduced by 26%, 27.5% and 27%, respectively. This implies that the design scale of the equipment can be notably decreased. The energy consumption of the equipment is $22326 \times 10^6$ J/ton of (p-xylene+benzene), which is reduced by 16% in relative to the energy consumption of $26579 \times 10^6$ J/ton of (p-xylene+benzene) in Comparison Example 1. Thus, the present invention overcomes the problems suffered by the existing techniques for the production of p-xylene that the concentration of p-xylene in mixed xylenes is low, that circulation quantity is large, and that energy consumption is high, and provides a new and economical process for the production of p-xylene.

TABLE 11

Materials in the process of Example 5

| Components | | Selective disproportionation unit | $C_9^+A$ dealkylation unit | Isomerization unit |
|---|---|---|---|---|
| Feed to the unit, Kg/hr | Ben | 14 | 0 | 0 |
| | Tol | 97617 | 0 | 108 |
| | $C_8A$ | 92 | 211 | 161632 |
| | $C_9A$ | 0 | 36715 | 87 |
| | $C_{10}^+A$ | 0 | 1824 | 0 |
| | Σ | 97723 | 38750 | 161827 |
| Discharge from the unit, Kg/hr | Ben | 13502 | 2 | 2069 |
| | Tol | 67233 | 5900 | 1038 |
| | PX | 12086 | 12011 | 155995 |
| | $C_8A*$ | 1622 | | |
| | $C_9A$ | 791 | 14020 | 869 |
| | $C_{10}^+A$ | 0 | 3036 | 0 |
| | Σ | 95234 | 34969 | 157902 |

TABLE 12

Processing scales of various units in Example 5

| Name of unit | $C_9^+A$ dealkylation unit | Isomerization unit | Adsorption separation unit | Crystallization separation unit | Aromatic hydrocarbon fractionation unit |
|---|---|---|---|---|---|
| Scale, Kg/hr | 38750 | 162546 | 197362 | 13708 | 235861 |

TABLE 13

Yield and purity of products in Example 5

| Product | p-xylene | Benzene | In total |
|---|---|---|---|
| Yield, Kg/hr | 49258 | 29066 | 78324 |
| Purity, % | 99.80 | 99.94 | |

Example 6

This experiment was performed by following the procedure as described in Example 5, except that the $C_8A$ obtained by separating the product of the toluene selective disproportionation reaction in an aromatic hydrocarbon fractionation unit was sent to a suspension crystallization separation unit to recover p-xylene. The conditions for the suspension crystallization separation were the same as described in Example 2. The processing scales of various units in the equipment for the production of p-xylene are listed in Table 14. The yields of p-xylene and benzene as products are listed in Table 15.

TABLE 14

Processing scales of various units in Example 6

| Name of unit | $C_9^+A$ dealkylation unit | Isomerization unit | Adsorption separation unit | Crystallization separation unit | Aromatic hydrocarbon fractionation unit |
|---|---|---|---|---|---|
| Scale, g/hr | 38750 | 162546 | 197362 | 13708 | 235861 |

TABLE 15

Yield and purity of products in Example 6

| Product | p-xylene | Benzene | In total |
|---|---|---|---|
| Yield, Kg/hr | 49258 | 29067 | 78325 |
| Purity, % | 99.80 | 99.94 | |

The results demonstrate that, by using the present process, it is possible to use the aromatic hydrocarbon feedstock as listed in Table 5 to produce p-xylene and benzene at a total yield of the both of 78325 Kg/hr. As compared with the Comparative Example 1 below, the processing scales of xylene isomerization unit, adsorption separation unit and aromatic hydrocarbon fractionation unit are reduced by 22%, 26% and 24%, respectively. This implies that the design scale of the equipment can be notably decreased. The energy consumption of the equipment is $22060 \times 10^6$ J/ton of (p-xylene+benzene), which is reduced by 17% in relative to the energy consumption of $26579 \times 10^6$ J/ton of (p-xylene+benzene) in Comparison Example 1.

Comparative Example 1

A typical reformed depentanized oil containing $C_6A$ to $C_{10}^+$ hydrocarbons was used as a feedstock to investigate the capacities of the prior art process as shown in FIG. 1 for the production of p-xylene and benzene as well as the processing scales of various units therein. The composition of the reformed depentanized oil and the flow rates of various components used in this Example are listed in Table 5. The data regarding feed and discharge for disproportionation and transalkylation unit and for isomerization unit are listed in Table 16. The processing scales of various units are listed in Table 17. The yields of p-xylene and benzene as products are listed in Table 18.

TABLE 16

Materials in the process of Comparative Example 1

| | Components | Disproportionation and transalkylation unit | Isomerization unit |
|---|---|---|---|
| Feed to the unit, Kg/hr | Ben | 12 | 0 |
| | Tol | 65630 | 0 |
| | $C_8A$ | 332 | 219340 |
| | $C_9A$ | 42789 | 98 |
| | $C_{10}^+A$ | 3225 | 0 |
| | Σ | 111988 | 219438 |
| Discharge from the unit, Kg/hr | Ben | 9035 | 420 |
| | Tol | 40223 | 1883 |
| | $C_8A$ | 33919 | 210585 |
| | $C_9A$ | 18590 | 3175 |
| | $C_{10}^+A$ | 4527 | 0 |
| | Σ | 106294 | 216063 |

TABLE 17

Processing scales of various units in Comparative Example 1

| Name of unit | Disproportionation and transalkylation unit | Isomerization unit | Adsorption separation unit | Xylene fractionation unit |
|---|---|---|---|---|
| Scale, Kg/hr | 111988 | 219438 | 274572 | 323269 |

TABLE 18

Yield and purity of products in Comparative Example 1

| Product | p-xylene | Benzene | In total |
|---|---|---|---|
| Yield, Kg/hr | 54316 | 22751 | 77067 |
| Purity, % | 99.80 | 99.94 | |

The results show that, according to the conventional process for the production of aromatic hydrocarbons, it is possible to use the aromatic hydrocarbon feedstock as listed in Table 5 to produce p-xylene and benzene at a total yield of the both of 77067 Kg/hr and at an energy consumption of $26579 \times 10^6$ J/ton of (p-xylene+benzene).

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

We claim:

1. An integrated process for the production of p-xylene, comprising the steps of:
    A) separating a mixed feedstock containing benzene, toluene, $C_8$ aromatic hydrocarbons, $C_9$ and higher aromatic hydrocarbons, and non-aromatic hydrocarbons from a reforming unit, to obtain a first benzene stream, a first toluene stream, a first $C_8$ aromatic hydrocarbon stream, a stream of $C_9$ and higher aromatic hydrocarbons, and a stream of non-aromatic hydrocarbons;
    B) feeding the stream of $C_9$ and higher aromatic hydrocarbons from step A) to a $C_9$ and higher aromatic hydrocarbon dealkylation unit, where dealkylation reaction occurs in the presence of hydrogen, and separating the reaction effluent to obtain a second benzene stream, a second toluene stream, and a second $C_8$ aromatic hydrocarbon stream;
    C) feeding both the first toluene stream and the second toluene stream to a toluene selective disproportionation unit, where toluene selective disproportionation reaction occurs in the presence of hydrogen to produce a stream containing $C_8$ aromatic hydrocarbons including p-xylene and benzene, which stream is separated to obtain a third $C_8$ aromatic hydrocarbon stream, a third toluene stream, and a third benzene stream, with the third toluene stream being returned to an inlet of this unit;
    D) feeding both the first $C_8$ aromatic hydrocarbon stream and the second $C_8$ aromatic hydrocarbon stream to an adsorption separation unit, to obtain a first p-xylene product stream and a fifth $C_8$ aromatic hydrocarbon stream, with the fifth $C_8$ aromatic hydrocarbon stream being passed to an isomerization unit;
    E) feeding the third $C_8$ aromatic hydrocarbon stream to a crystallization separation unit, to obtain a fourth $C_8$ aromatic hydrocarbon stream and a second p-xylene product stream, with the fourth $C_8$ aromatic hydrocarbon stream being passed to the adsorption separation unit or the isomerization unit; and
    F) feeding an effluent of the isomerization unit to an inlet of the adsorption separation unit.

2. The integrated process of claim 1, wherein the catalyst used in the toluene selective disproportionation unit is a ZSM-5 molecular sieve catalyst containing at least one metal selected from the group consisting of platinum, molybdenum and magnesium and/or oxides thereof in an amount of from 0.005 to 5% by weight.

3. The integrated process of claim 1, wherein the toluene selective disproportionation unit is operated under the following conditions: a reaction pressure of from 1 to 4 MPa, a reaction temperature of from 300 to 480° C., a molar ratio of hydrogen to hydrocarbons of from 0.5:1 to 10:1, and a weight hourly space velocity of from 0.8 to 8 $hr^{-1}$.

4. The integrated process of claim 1, wherein the catalyst used in the $C_9$ and higher aromatic hydrocarbon dealkylation unit is a molecular sieve catalyst containing bismuth and/or its oxide in an amount of from 0.005 to 5% by weight, wherein the molecular sieve is at least one selected from the group consisting of β-zeolite, mordenite and MCM-22.

5. The integrated process of claim 1, wherein the $C_9$ and higher aromatic hydrocarbon dealkylation unit is operated under the following conditions: a reaction pressure of from 1 to 5 MPa, a reaction temperature of from 250 to 480° C., a molar ratio of hydrogen to hydrocarbons of from 0.5:1 to 8:1, and a weight hourly space velocity of from 0.8 to 10 $hr^{-1}$.

6. The integrated process of claim 1, wherein the crystallization separation of p-xylene is conducted by means of falling-film crystallization separation or suspension crystallization separation.

7. The integrated process of claim 6, wherein the falling-film crystallization separation is conducted at a crystallization temperature of from −80 to 5° C.; and in the suspension crystallization separation, the crystallization temperature is from −80 to 5° C., and a weight ratio of washing liquid to crystal is from 0.05:1 to 0.5:1.

8. The integrated process of claim 1, wherein at least a portion of the second benzene stream obtained in step B) is returned to an inlet of the aromatic hydrocarbon dealkylation unit.

* * * * *